United States Patent [19]
Mikhail

[11] Patent Number: 5,180,384
[45] Date of Patent: Jan. 19, 1993

[54] METHOD FOR IMPLANTING A PATELLAR PROSTHESIS

[76] Inventor: W. E. Michael Mikhail, 4203 Shamley Green, Toledo, Ohio 43623

[21] Appl. No.: 652,882

[22] Filed: Feb. 8, 1991

[51] Int. Cl.⁵ .............................................. H61F 5/04
[52] U.S. Cl. ...................... 606/80; 623/20; 606/79
[58] Field of Search ............... 623/16, 18, 20, 22, 623/23; 606/80, 88, 96

[56] References Cited

U.S. PATENT DOCUMENTS

| | | |
|---|---|---|
| 3,878,566 | 4/1975 | Bechtol . |
| 4,158,894 | 6/1979 | Worrell . |
| 4,341,206 | 7/1982 | Perrett et al. ........................ 606/96 |
| 4,686,972 | 8/1987 | Kurland . |
| 4,860,735 | 8/1989 | Davey et al. . |
| 4,919,673 | 4/1990 | Willert . |
| 4,919,679 | 4/1990 | Averill . |
| 4,982,730 | 1/1991 | Lewis, Jr. .......................... 604/22 |

OTHER PUBLICATIONS

"Surgical Procedure for the Whiteside Ortholoc Modular Knee System", Dow Corning Wright.
Article entitle "Economy is the Mother of a Cement Removal Technique", Orthopedics Today, pp. 18 and 19, Sep. 1989.
Brochure published by Johnson & Johnson Orthopaedics entitled "Patellar Resurfacing with Specialist® Instruments in Total Knee Arthroplasty-Surgical Technique".
Brochure published by Dow Corning Wright entitled "Whiteside Ortholoc® Modular Knee System".
Brochure published by Dow Corning Wright entitled "Surgical Procedure for the Whiteside Ortholoc® Modular Knee System".
Brochure published by Intermedics Orthopedics entitled "Surgical Technique—The Intermedics Natural-Knee System".
Brochure published by DePuy, Division of Boehringer Mannheim Corporation, Warsaw, Ind., p. 25.

Primary Examiner—David Isabella
Assistant Examiner—Gina M. Gualtieri
Attorney, Agent, or Firm—Emch, Schaffer, Schaub & Porcello Co.

[57] ABSTRACT

A method for preparing a patella for receiving a patellar implant and for implanting a prosthesis therein. An elongated passageway is formed in the patella which is then reamed to form a cavity of a size and configuration to receive the patellar prosthesis using a cannulated reamer telescoped over a guide rod positioned in the elongated passageway.

12 Claims, 4 Drawing Sheets

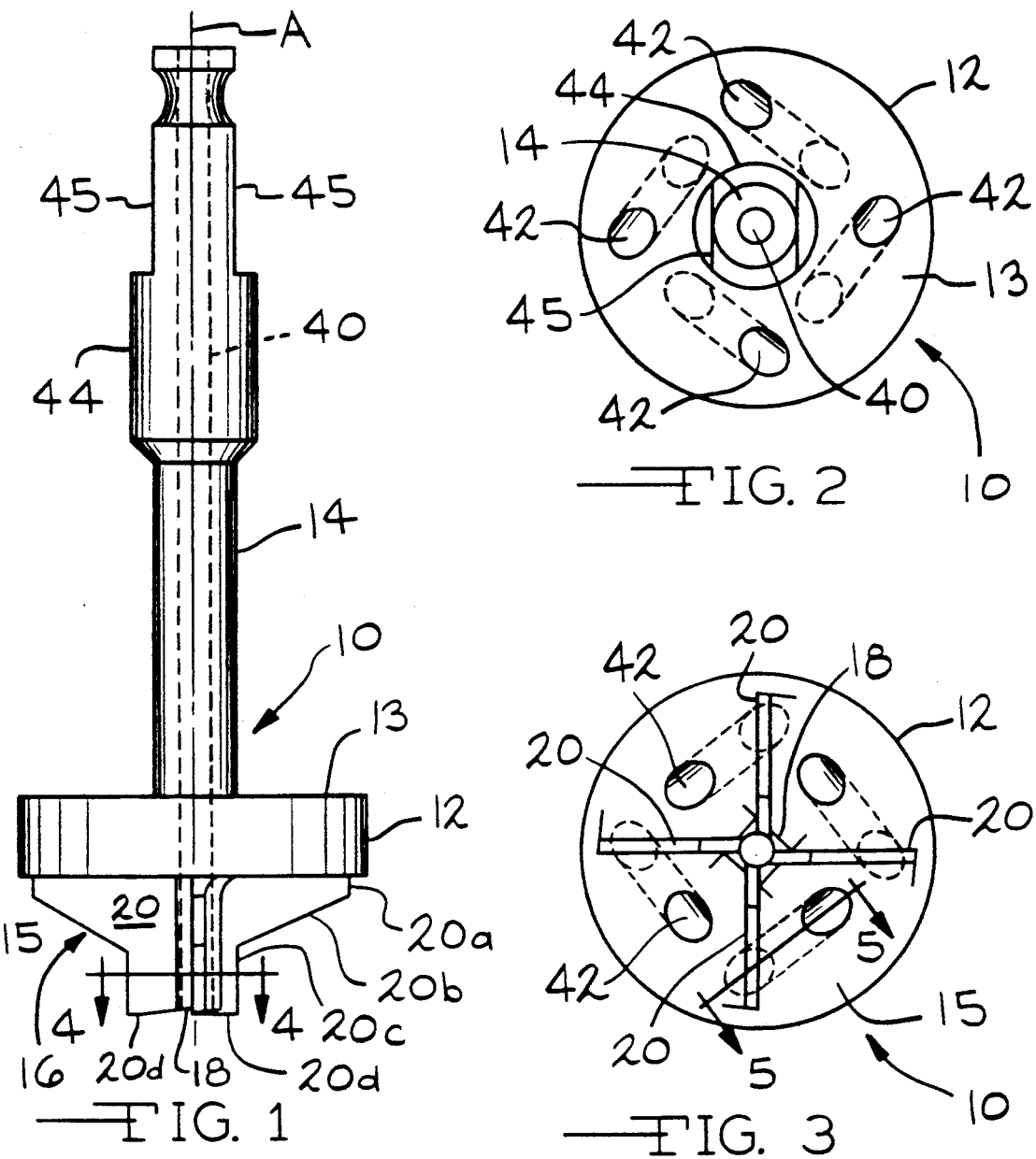
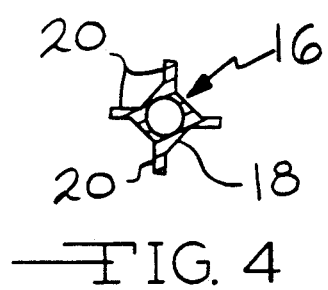
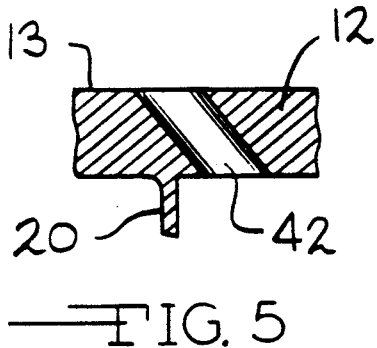

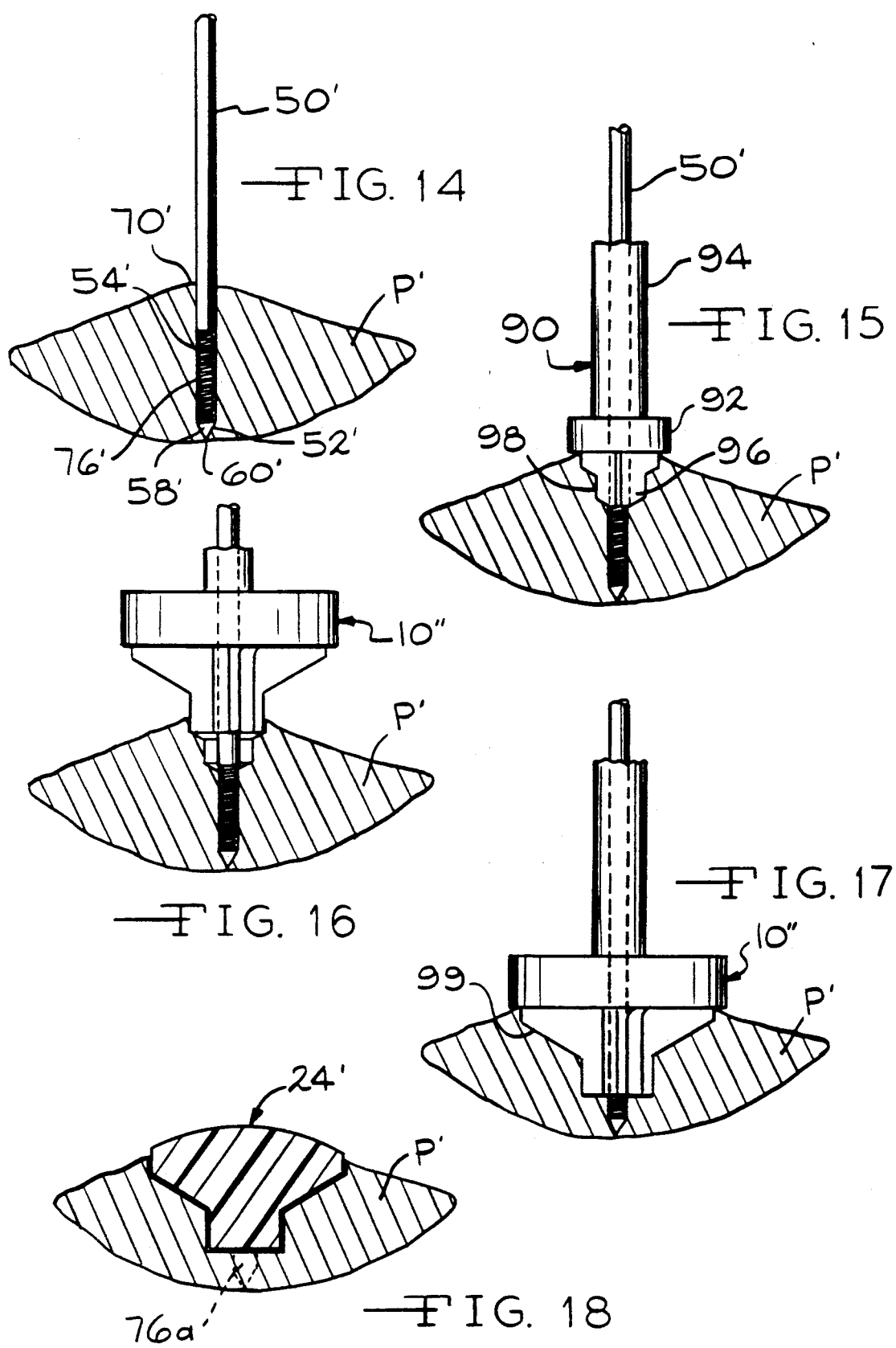

METHOD FOR IMPLANTING A PATELLAR PROSTHESIS

BACKGROUND OF THE INVENTION

The present invention is directed to a method for implanting a patellar prosthesis in a human patella.

In total knee replacement surgery, a prosthesis is provided in which one component is fastened to the distal end of the femur which has been resectioned and another component is fastened to the proximal end of the tibia which has been resectioned so that the two components will act together in permitting the leg to bend and straighten out. In performing such surgery, the patella is not normally replaced but rather is resected such that the interior crown portion facing the condyles is cut and reamed to form a cavity in which a patella prothesis is implanted. The patellar prosthesis has a crown facing inwardly to engage the patellar or trochlear groove of the femoral component.

Heretofore, in preparing a patella for an implant, it was necessary to engage the patella with a clamp having a circular cross-sectional configuration and, using the interior surface of the clamp as a guide, ream a cavity in the patella of sufficient size to receive the patellar implant intended to be used. Depending upon a number of factors including the size of the patient, the patellar implant could be one of a number of different sizes. As a result of this, it was necessary to have available a number of clamps each having a different diameter for guiding various size reamers. Typical prior art methods of forming a cavity for implanting a patellar prosthesis are shown and described in the following publications, which are incorporated herein by reference: Brochures entitled "The AMK Total Knee System Design Rationale and Surgical Procedure" (page 25), DePuy, Division of Boehringer Mannheim Corporation, Warsaw, Ind., and "WHITESIDE ORTHOLOC® Modular KNEE SYSTEM", copyright 1989 by Dow Corning Wright, Arlington, Tenn. Copies of such references are herewith enclosed.

There has recently been introduced a new design of patellar prosthesis is the subject matter of U.S. Patent application Ser. No. 07/508,088, filed Oct. 18, 1990, by the applicant herein. The present method for implanting a patellar prosthesis is well-suited for implanting patellar prostheses of the type disclosed in such patent application; however, it should be understood that the method of the present invention is not so limited and may be used for implanting a wide variety of patellar prostheses. It has a significant advantage over the prior art for implanting a patellar prosthesis of a type in which one of a number of different sizes is to be used depending upon the patient in that the method of the present invention does not rely upon the patella clamp to guide the reamer. Accordingly, in utilizing the method of the present invention, it is not necessary to have available a plurality of clamps of varying sizes.

SUMMARY OF THE INVENTION

The present invention provides a new method for preparing a human patella for implanting a patellar prosthesis therein and a new method for implanting a patellar prosthesis in a human patella. As is well-known in performing knee replacement surgery, the patella is everted and retained in a position permitting the surgeon to have access to the articular surface which is normally engaged in the intercondylar notch between the condyles. Under the present invention, with the patella so supported, the surgeon, using a saw or similar tool for performing osteotomy, removes the top portion of the articular surface, thus leaving a flat surface near the central portion of the patella. Desirably, only a small portion of the articular surface is removed in order to leave as much of the original patella intact as possible. Thus, as pointed out in the above-identified patent application, it is desirable that as little of the human patella be removed as possible.

Following removal of the top of the articular surface a thread guidewire or pin is used to drill a passageway in the central portion of the patella at substantially right angles to the flat surface. Then, using the threaded guidewire which may be left in the passageway or a rod similar size to that of the threaded guidewire positioned in said passageway, a cannulated reamer is placed over the threaded guidewire or other guide rod and, using such threaded guidewire or guide rod as a guide, the reamer is utilized to ream the patella thereby forming a cavity having a size and configuration suitable for receiving the patellar prosthesis. Following such reaming, the cavity is cleaned, bone cement placed therein and the patellar prosthesis implanted therein. If desired, the reaming could be performed in stages, initially using a reamer sized to form a relatively small cavity and thereafter using a reamer sized to form the cavity for receiving the patella prosthesis.

It is also within the contemplation of the present invention to drill the passageway without cutting the apex of the articular surface or otherwise forming a flat surface.

According, it is an object of the present invention to provide a method for implanting a patellar prosthesis in a human patella.

It is a further object of the present invention to provide a method of cutting and reaming a patella in preparation for implanting a patellar prosthesis to provide accurate positioning while minimizing the amount of bone required to be removed.

It is a further object of the present invention to provide a method for preparing a patella for implantation of a patellar prosthesis without the necessity of using a patellar clamp for guiding the reamer.

Other objects and advantages of the present invention will become apparent from the following detailed description in conjunction with the attached drawings.

BRIEF DESCRIPTION OF THE DRAWINGS

FIG. 1 is an elevational view showing a cannulated reamer having cutting knives of a configuration suitable for implanting one type of patellar prosthesis.

FIG. 2 is a top plan view of the cannulated reamer of FIG. 1.

FIG. 3 is a bottom plan view of the cannulated reamer of FIG. 1.

FIG. 4 is a sectional view taken along line 4—4 of FIG. 1.

FIG. 5 is a fragmentary sectional view of the reamer head taken along line 5—5 of FIG. 3.

FIG. 14 is a sectional view of a patella during the initial step of a modified method of preparing a patella wherein a passageway is formed without first forming a flat surface.

FIG. 15 is a view similar to FIG. 14 showing one of a plurality of reaming steps using the threaded guidewire or other guide rod to guide the reamer during reaming.

FIG. 16 is a view similar to FIG. 15 showing the second reamer beginning to ream the final cavity.

FIG. 17 is a view similar to FIG. 16 showing completion of reaming the final cavity.

FIG. 18 is a sectional view showing a patellar prosthesis implanted in a patella prepared in accordance with the present invention.

DESCRIPTION OF THE PREFERRED EMBODIMENT

Figure 8:
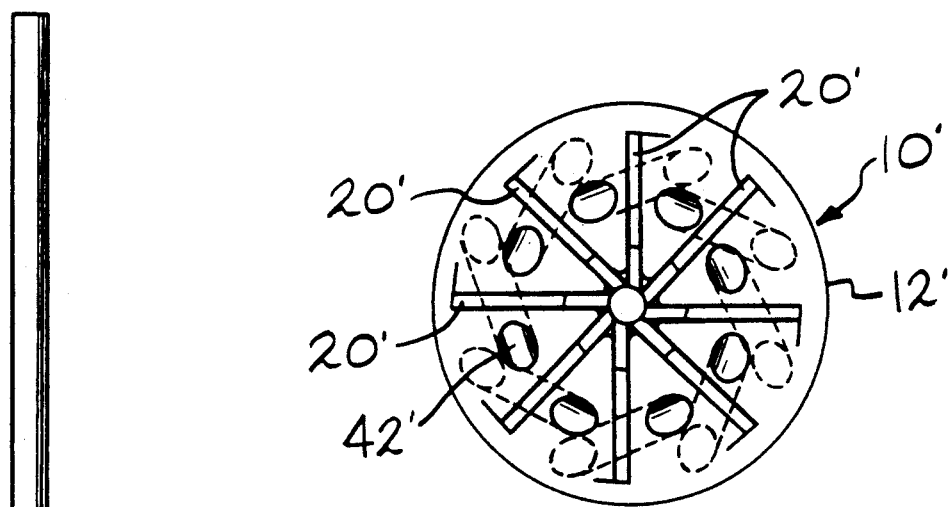
FIG. 8 is a view similar to FIG. 3 showing a modified reamer.

Referring now to FIGS. 1-5, there is shown a reamer generally designated by numeral 10 having a head 12 mounted on the end of a cannulated stem 14 extending along an axis A. The head 12 has an upper surface 13 and a lower surface 15. A cutting assembly 16 extends downwardly from the head 12 and includes a housing 18 and a plurality of cutting blades 20 integrally formed with and extending radially outwardly from the housing 18. In the embodiment of FIGS. 1-5, four cutting blades 20 are provided at substantially 90° from each other. As can be seen particularly in FIG. 1, the shape of the cutting blades are substantially identical and have a configuration tailored to form a cavity of a size and shape suitable for receiving the specific patellar prosthesis intended for implantation.

Figure 13:
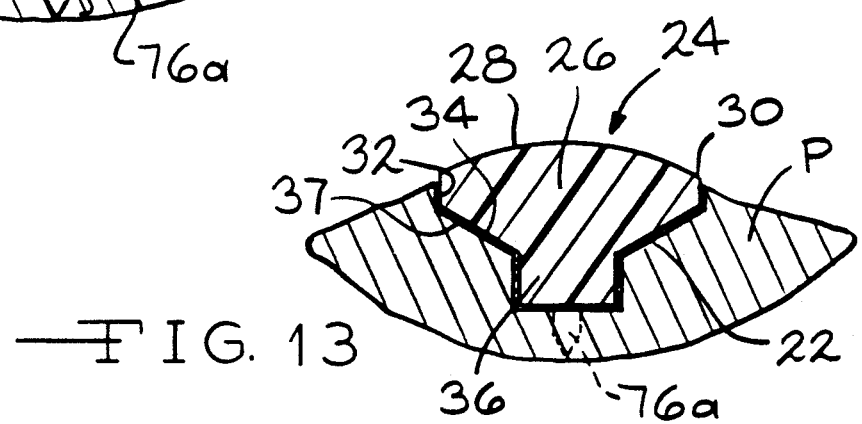
FIG. 13 is a sectional view showing a patellar prosthesis implanted in a patella prepared in accordance with the present invention.

For example, referring briefly to FIG. 13, there is shown a patella P in which a cavity 22 has been reamed and in which a patellar prosthesis 24 has been implanted utilizing the method of the present invention. The patellar prosthesis 24 of FIG. 13 has a body portion 26 with a dome 28 facing away from the patella P in a position to engage the patellar or trochlear groove of the femoral component of a total knee implant (not shown). The dome 28 terminates at its outer periphery at an edge 30 which defines a circle from which a short cylindrical wall section 32 depends. As can be seen in FIG. 13 the edge 30 is preferably above the upper surface of the patella P about 1-2 mm; however, it could meet the upper surface of the patella and thus provide a smooth transition between the dome 28 and the upper surface of the patella P.

Tapering inwardly toward the central axis and downwardly in a direction away from the dome 28 is an inner wall surface 34 from which a stem 36 depends. The stem 36 may have one of a wide variety of shapes including the shapes shown in the brochures identified on page 1 hereof or the shape shown in my co-pending application Ser. No. 07/508,088 filed Oct. 18, 1990. A layer of bone cement 37 such as polymethylmethacrylate is used to bond the patellar prosthesis 24 in the cavity.

As will be appreciated from viewing FIG. 1 and FIG. 13, the cross-sectional shape of that portion of the patellar prosthesis 24 facing away from the dome 28 determines the shape defined by the cutting blades 20 and the shape of the cavity to be formed thereby. Thus, each of the blades 20 has a first cutting edge 20a substantially parallel to the axis A of the stem 14, a second cutting edge 20b tapering inwardly toward such axis A and away from the head 12, a third cutting edge 20c substantially parallel to such axis and a fourth cutting edge 20d extending radially inwardly from the third cutting edge 20c and joined to the housing 18. It should be understood, however, that the shape of the cutting blades 20 may vary depending upon the configuration of the patellar prosthesis intended to be implanted. In forming a cavity of the configuration shown in FIGS. 12 and 13 for receiving the prosthesis 24, the third cutting edge 20c and fourth cutting edge 20d will form a lower cylindrical portion of the cavity 22 intended to receive the stem 36, the second cutting edge 20b will form the portion of the cavity 22 flaring upwardly and outwardly from the lower cylindrical portion for receiving the portion of the prosthesis defined by the tapering inner wall surface 34 and the first cutting edge 20a will form the upper cylindrical portion of the cavity 22 for receiving the short cylindrical wall section 32 of the patellar prosthesis 24.

Figure 12:
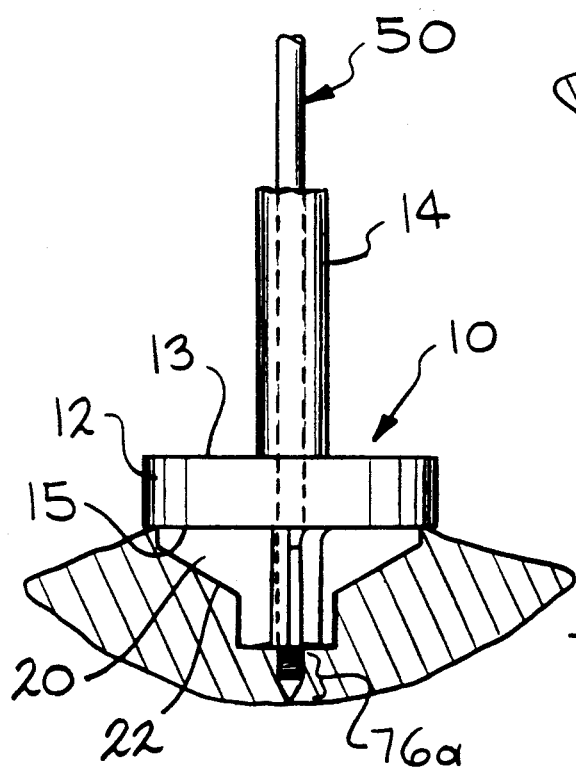
FIG. 12 is a view similar to FIG. 11 showing the reaming step using the drill bit or other guide rod to guide the reamer during reaming.

As can be seen in FIGS. 1 and 12, the cutting blades 20 do not extend outwardly to the outer periphery of the head 12. Thus, the first cutting edge 20a is closer to the axis A than is the outer periphery of the head 12. This construction permits the lower surface 15 to contact the patella P and function as a stop for determining the proper depth for the cavity 22 and insure against inadvertent reaming to an excessive depth.

The reamer 10 has a cylindrical passageway 40 extending throughout the stem 14, head 12 and housing 18. Additionally, the head 12 has a plurality of inclined passageways 42 extending therethrough from a position on the lower surface 15 between the cutting blades 20 and extending out of the upper surface 13. These inclined passageways 42 are intended to provide a means for expelling the debris from the cavity 22 being reamed. Thus, as the blades 20 ream the patella P, the bone material cut therefrom will be propelled into the end of the inclined passageway 42 at the lower face 15, through the inclined passageway 42 and out of it at the upper face 13.

The stem 14 of the reamer 10 has an enlarged area 44 which may be provided with opposing flat surfaces 45 for engagement by rotatable power means for rotating the head 12 and the cutting blades 20 carried thereby.

Figure 6:
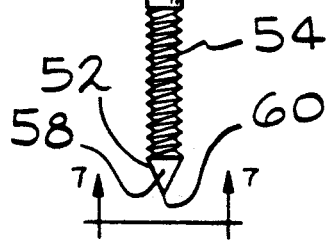
FIG. 6 is an elevational view showing the threaded guidewire for forming a guide passageway in the patella.
Figure 7:
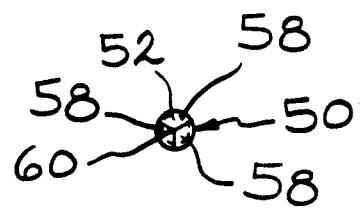
FIG. 7 is an end view of the threaded guidewire of FIG. 6 looking in the direction of the arrows 7—7.

Referring now to FIGS. 6 and 7, there is shown a threaded guidewire 50 having a cutting head 52, a helical thread 54 and an enlongated shank 56 having a diameter slightly smaller than that of the cylindrical passageway 40 and a length sufficiently long to extend completely through the stem 14 of reamer 10. The cutting head 52 has three triangular shaped flats 58 extending to a trip 60 with the edges between the adjoining flats 58 functioning as the primary cutters.

Figure 9:
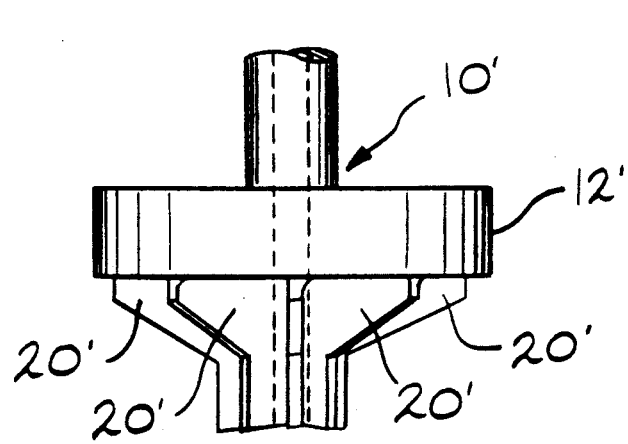
FIG. 9 is a fragmentary elevational view of the modified reamer of FIG. 8.

FIGS. 8 and 9 show a modified reamer 10' having a head 12' with eight cutting blades 20' as contrasted with the previous embodiment having four cutting blades 20.

In this embodiment, there are provided eight inclined passageways 42' extending through the head for expelling debris during the cutting operation.

Figure 10:
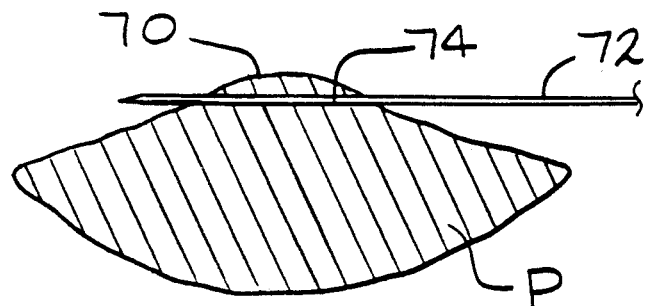
FIG. 10 is a sectional view of a patella during the initial step of removing the apex of the articular surface to form a flat surface.
Figure 11:
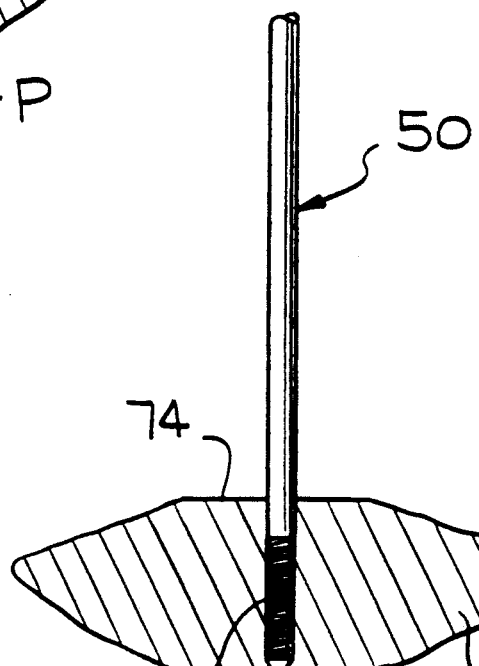
FIG. 11 is a view similar to FIG. 10 showing the next step of drilling a passageway at substantially right angles to the flat surface formed as shown in FIG. 10.

Referring now to FIGS. 10-12, there is shown a human patella P having an articular surface including an apex 70 which, in a normal knee prior to surgery, engages the intercondylar notch between the condyles at the distal end of the femur. According to the method of the present invention, the top of the apex 70 is cut with a standard cutting blade 72 to form a substantially planar surface 74 as shown in FIGS. 10 and 11. Thereafter, the threaded guidewire 50 powered by a drill (not shown) is utilized to drill a passageway 76 in the patella P.

Following drilling of the passageway 76 of the drill is disconnected from the threaded guidewire 50, leaving the threaded guidewire 50 in the passageway 76. Then, using the threaded guidewire 50 as a guide, the reamer 10 is placed thereover and is connected to power means which rotates it thereby causing the cutting blades 20 to form the cavity 22 having a configuration determined by the configuration of the cutting edges 20a, 20b, 20c and 20d of cutting blades 20. In the drawings it is shown as having the desired configuration to receive the patellar prosthesis 24. During such cutting the threaded guidewire 50, snugly received in the passageway 40, serves to accurately guide the reamer 10 on the correct axial path in reaming the patella P to form the cavity 22. Thus, the threaded guidewire 50 prevents the reamer 10 from drifting off such path and forming a larger cavity than desired. As previously noted, during such reaming process, debris will be expelled through the included passageways 42 extending through the head 12. Competion of the reaming step occurs when the lower surface 15 of the head 10 engages the patella P. As previously noted, the design of the reamer head 12 to cause engagement of such lower surface 15, prevents the reamer from reaming to a greater depth than desired.

Following completion of the reaming step, the reamer 10 and the threaded guidewire 50 are removed, the cavity 22 is cleaned of debris and prepared in accordance with standard surgical implantation techniques including application of bone cement such as polymethylmethacrylate and affixing of the patellar prosthesis 24 therein. Preferably, prior to placing bone cement in the cavity 22, pulverized bone clips and/or bone slurry will be placed in the end portion 76a of the passageway 76 extending below the bottom of that portion of the cavity 22 formed by the lower cutting edge 20d. Such bone chips and/or bone slurry serve as a graft inducing bone growth into such end portion 76a. However, it is possible that such end portion be filled only with bone cement.

Irrespective of whether the cutting head has four cutting blades 20 shown in the embodiment of FIGS. 1-5, or eight cutting blades 20' shown in the embodiment of FIGS. 8 and 9 or fewer or more of such cutting blades, the method set forth pursuant to the present invention permits the implantation of a patellar prosthesis in a highly accurate manner with a minimal removal of bone.

Referring now to FIGS. 14-18, there is shown a modified method for preparing a patella P' and for implanting a patellar prosthesis 24' therein.

As shown in FIG. 14, there is provided a threaded guidewire 50' having a head 52' with cutting flats 58' extending to a tip 60'. A helical thread 54' extends upwardly from the head 52'.

Under this embodiment, the apex 70' of the patella P' is not cut to form a flat surface as in the previous embodiment, but rather the threaded guide wire 50' directly engages the articular surface at a desired location in the vicinity of the apex 70. As will be appreciated by those skilled in the art, during this step, the patella P' will be held by a suitable clamping mechanism while the drill powering the threaded guidewire 50' is used to form a passageway 76' in the patella P'.

The drill is then disconnected from the threaded guidewire 50' and a first or pilot reamer 90 having a head 92 mounted on the end of a cannulated stem 94 is positioned over the threaded guidewire 50'. The head 92 has a plurality of cutting blades 96 extending downwardly therefrom. As can be seen from FIG. 15, the head 92 and cutting blades 96 of the pilot reamer 90 are much smaller than required to form a cavity of the size intended for the patellar implant 24' as shown in FIG. 18. Thus, the first or pilot reamer 90 forms a relatively small cavity 98. As shown in FIGS. 16 and 17, a second reamer 10'' similar or identical to the reamer 10 of the embodiment of FIGS. 1-5 is provided to form a final cavity 99 having a size and configuration suitable for receiving the patellar implant 24'. It may be preferable to the surgeon to perform the reaming in two steps, particularly if the surgeon does not wish to form the flat surface by cutting the apex of the articular surface. In performing the reaming in two steps, the surgeon forms first a relatively small cavity 98 using the threaded guidewire 50' or other guide means positioned in the passageway 76' to guide the direction of the first or pilot reamer 90 and thereafter forming the final cavity 99 with reamer 10' again using the threaded guidewire 50' or other guide means. As in the previous embodiments the end portion 76a is preferably filled with bone chips or bone slurry to serve as a graft inducing bone growth therein.

Although the method has been described using a cannulated reamer 10 with flat cutting blades 20, it should be understood that a wide variety of reamers could be used. For example, a convex grater type reamer with a cannulated center to accomodate the guide wire is one which could be used.

Many modifications and embodiment will become readily apparent to those skilled in the art. Accordingly, the scope of the present invention should be determined only by the scope of the appended claims.

I claim:

1. A method of planting a patellar prosthesis in a human patella having an articular surface with an apex comprising:
    (a) providing a patellar prosthesis having a body portion including an upper dome and a lower stem on the opposite side of said body portion from said dome;
    (b) drilling a passageway in said patella inwardly from the side having said articular surface;
    (c) providing elongated guide means in said passageway;
    (d) providing a reamer having a head with upper and lower sides, cutting means depending from said lower side and a central cannulation extending through said cutting means and said head, said cannulation having a size to fit over said guide wire, said head having a plurality of apertures extending therethrough from said lower to said upper side;

(e) positioning said reamer over said elongated guide means and reaming a cavity in said patella having a size and configuration to receive said patellar prosthesis while using said guide means as a guide to determine the position of said cavity and expelling debris formed during said reaming through the apertures in said head; and (f) placing said patellar prosthesis in said cavity in bonded relationship with said patella.

2. The method according to claim 1 further including the step of engaging said articular surface with stop means when said cavity has been reamed to the desired size.

3. The method according to claim 1, wherein said head has a lower face extending radially outwardly beyond said cutting means and further including the step of engaging said lower face against said articular surface to limit the depth of said reaming.

4. The method according to claim 1, wherein said reaming is performed in two steps including:

(a) reaming a first pilot cavity having a size smaller than the cavity intended for the patellar prosthesis; and, (b) reaming a second cavity to a size and configuration to receive said patellar prosthesis.

5. The method according to claim 1, wherein prior to step (b), said apex is removed to form a substantially planar surface.

6. A method of implanting a patellar prosthesis in a human patella having an articular surface with an apex comprising:

(a) providing a patellar prosthesis having a body portion including an upper dome and a lower stem on the opposite side of said body portion from said dome;

(b) engaging said patella with a clamp having an enlarged opening through which access to a central portion of said articular surface may be had;

(c) drilling a passageway in said patella inwardly from the side having said articular surface;

(d) providing elongated guide means in said passageway, said guide means extending through said clamp opening;

(e) providing a reamer having a head smaller than the enlarged opening of said clamp, cutting means depending from said head and a central cannulation extending through said cutting means and said head, said cannulation having a size to fit over said guide wire;

(f) positioning said reamer over said elongated guide means and reaming a cavity in said patella having a size and configuration to receive said patellar prosthesis while using said guide means as a guide to determine the position of said cavity, said reamer extending through said clamp enlarged opening throughout said step of reaming; and (g) placing said patellar prosthesis in said cavity in bonded relationship with said patella.

7. A method of implanting a patellar prosthesis in a human patella having an articular surface with an apex comprising:

(a) providing a patellar prosthesis having a body portion including an upper dome and a lower stem on the opposite side of said body portion from said dome;

(b) drilling a passageway in said patella inwardly from the side having said articular surface;

(c) providing elongated guide means in said passageway;

(d) providing a reamer having a head, cutting means depending from said head and a central cannulation extending through said cutting means and said head, said cutting means including a first portion adjacent said head, a second portion extending from said first portion having a cutting edge tapering inwardly toward said cannulation and away from said head, and a third portion extending from said second portion having a cutting edge substantially parallel to said cannulation; said cannulation having a size to fit over said guide wire;

(e) positioning said reamer over said elongated guide means and reaming a cavity in said patella having a cylindrical lower portion centered on said guide means and sized to receive said stem and an upper portion having a bottom wall tapering upwardly toward said articulating surface and outwardly from said guide means and sized to receive said body portion while using said guide means as a guide to determine the position of said cavity.

8. A method of implanting a patellar prosthesis in a human patella according to claim 7, wherein said cutting means first portion has a cutting edge substantially parallel to said cannulation and sized to cut said articular surface.

9. A method of implanting a patellar prosthesis in a human patella according to claim 7, wherein said reamer head has an upper side opposite the side from which said cutting means depend and aperture means extending therethrough to said upper side and further including the step of expelling debris formed during said reaming through said aperture means.

10. A method of preparing a patella having an articular surface with an apex for a patellar prosthesis implant comprising:

(a) forming an elongated passageway in said patella from said articular surface to a depth at least as deep as the depth intended for said patellar prosthesis;

(b) positioning elongated guide means in said passageway;

(c) positioning over said elongated guide means a cannulated reamer having a cannulation with the elongated guide means extending through said cannulation, said cannulated reamer having a head, cutting means depending from said head, said cutting means including a first portion adjacent head, a second portion extending from said first portion having a cutting edge tapering inwardly toward said cannulation and away from said head, and a third portion extending from said second portion having a cutting edge substantially parallel to said cannulation; and (d) reaming a cavity in said patella having a cylindrical lower portion centered on said guide means and sized to receive said stem and an upper portion having a bottom wall tapering upwardly toward said articulating surface and outwardly from said guide means and sized to receive said body portion while using said guide means as a guide to determine the position of said cavity.

11. A method of preparing a human patella according to claim 10, wherein said cutting means first portion has a cutting edge substantially parallel to said cannulation and sized to cut said articular surface.

12. A method of preparing a human patella according to claim 10, wherein said reamer head has an upper side opposite the side from which said cutting means depend and aperture means extending therethrough to said upper side offset from said cannulation and further including the step of expelling debris formed during said reaming through said aperture means.

* * * * *

UNITED STATES PATENT AND TRADEMARK OFFICE
CERTIFICATE OF CORRECTION

PATENT NO. : 5,180,384
DATED : January 19, 1993
INVENTOR(S) : W. E. Michael Mikhail It is certified that error appears in the above—identified patent and that said Letters Patent is hereby corrected as shown below:

Column 1, line 18, "patella" should read --patellar--.

Column 1, line 43, after the word "prosthesis" insert --having a tapered surface on the side away from the crown. One such prosthesis--.

Column 5, line 15, after "76" delete --of--.

Column 5, line 46, "clips" should read --chips--.

Column 6, line 50, "planting" should read --implanting--.

Signed and Sealed this

Thirtieth Day of November, 1993

Attest:

BRUCE LEHMAN

Attesting Officer

Commissioner of Patents and Trademarks